(12) United States Patent
Di Carlo et al.

(10) Patent No.: US 8,361,415 B2
(45) Date of Patent: Jan. 29, 2013

(54) INERTIAL PARTICLE FOCUSING SYSTEM

(75) Inventors: Dino Di Carlo, Los Angeles, CA (US);
Daniel R. Gossett, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/230,559

(22) Filed: Sep. 12, 2011

(65) Prior Publication Data

US 2012/0063971 A1 Mar. 15, 2012

Related U.S. Application Data

(60) Provisional application No. 61/382,300, filed on Sep. 13, 2010.

(51) Int. Cl.
*G01N 15/06* (2006.01)
*G01N 33/00* (2006.01)
*G01N 33/48* (2006.01)

(52) U.S. Cl. ......... 422/503; 422/50; 422/68.1; 422/502; 422/504; 422/509; 436/43; 436/63; 436/174; 436/180

(58) Field of Classification Search .................. 422/502, 422/503, 504, 509; 436/43, 174, 180
See application file for complete search history.

(56) References Cited

U.S. PATENT DOCUMENTS

| 7,964,078 | B2 | 6/2011 | Lee et al. |
| 2009/0014360 | A1 | 1/2009 | Toner et al. |
| 2010/0021984 | A1 | 1/2010 | Edd et al. |

FOREIGN PATENT DOCUMENTS

WO WO 2008/130977 A2 10/2008

OTHER PUBLICATIONS

Di Carlo, Dino et al., Equilibrium Separation and Filtration of Particles Using Differential Inertial Focusing, Anal. Chem. 2008, 80, 2204-2211.
Gossett, Daniel R. et al., Particle Focusing Mechanisms in Curving Confined Flows, Anal. Chem. 2009, 81, 8459-8465.

*Primary Examiner* — Brian J Sines
(74) *Attorney, Agent, or Firm* — Vista IP Law Group LLP

(57) ABSTRACT

An inertial particle focusing system for use with a particle having diameter (a) includes a curved microchannel into a substrate, said microchannel having a radius of curvature (r), and a channel hydraulic diameter ($D_h$), wherein the ratio of r to $D_h$ satisfies the following criterion:

$2ra^2/D_h^3 \geq 0.037$.

9 Claims, 6 Drawing Sheets

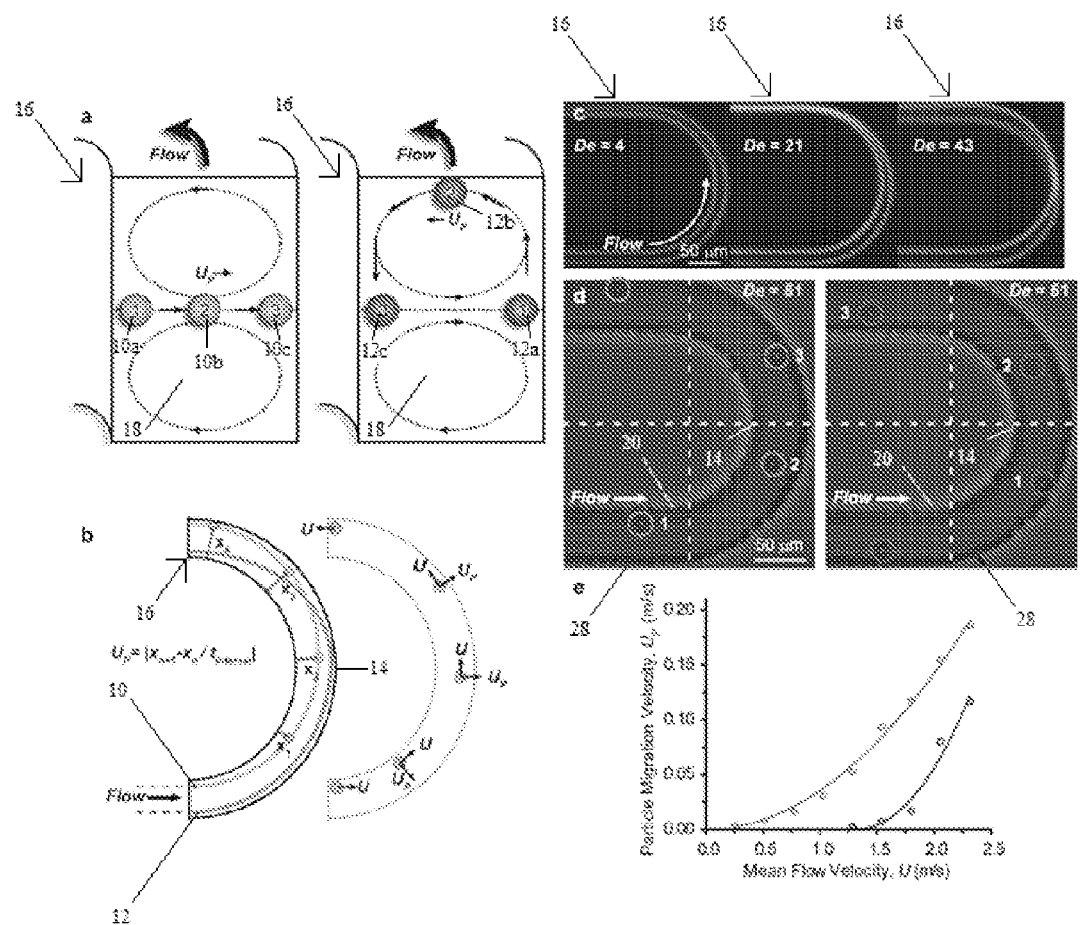
Figs. 1a-e

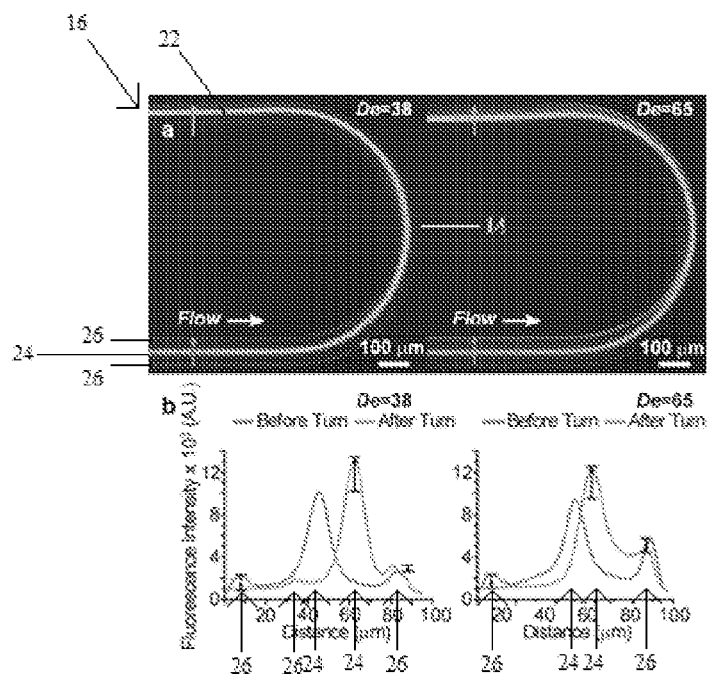
Figs. 2a-b
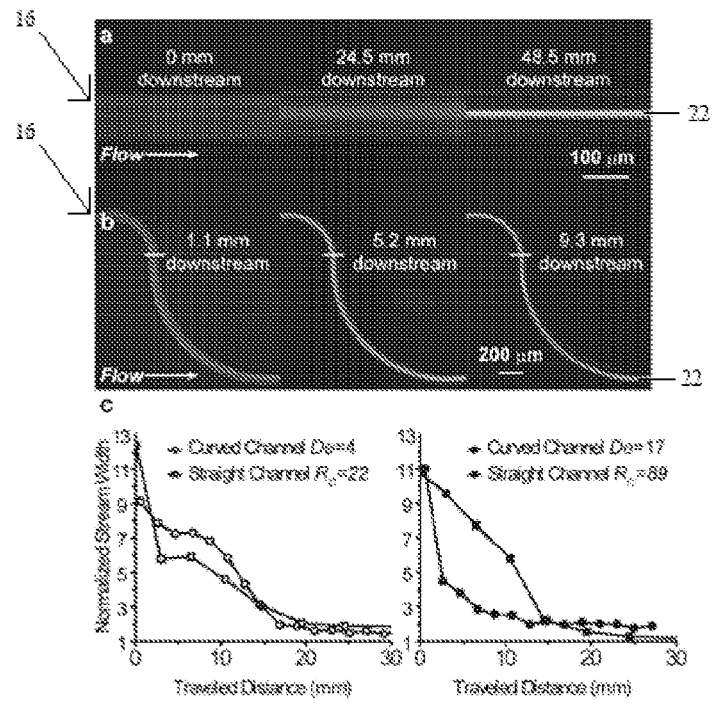
Figs. 3a-c

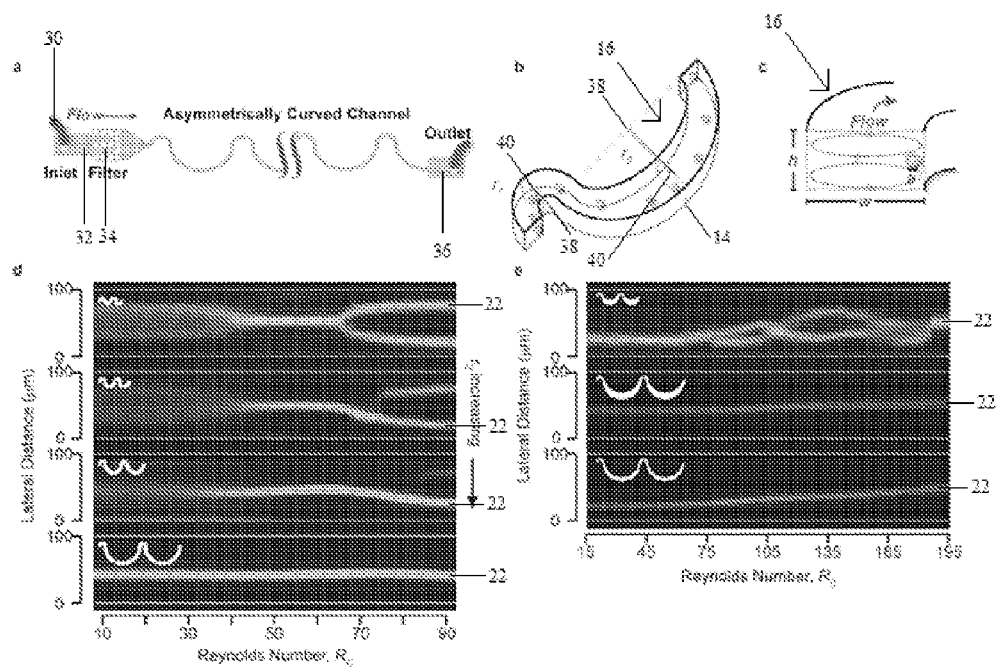
Figs. 4a-e
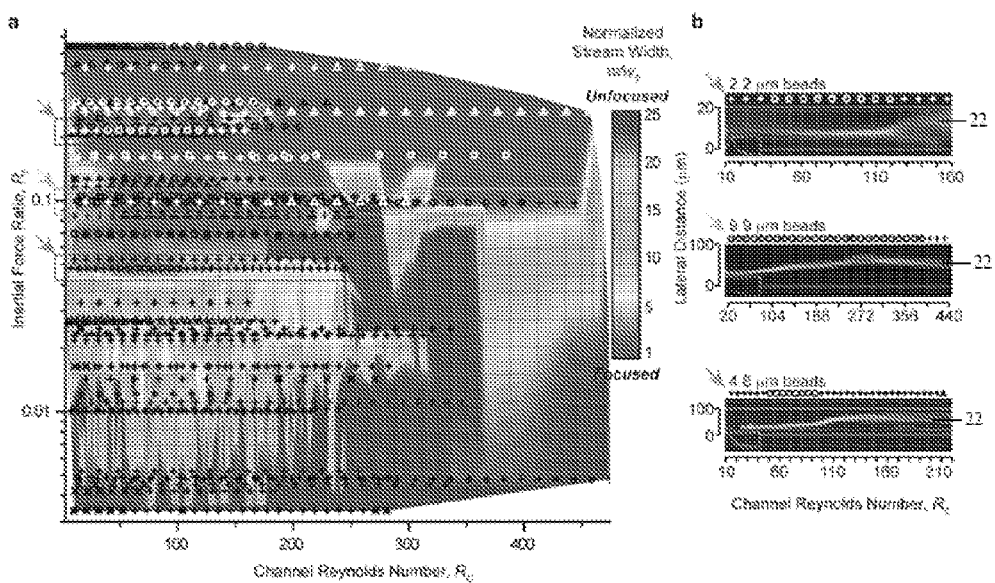
Figs. 5a-b

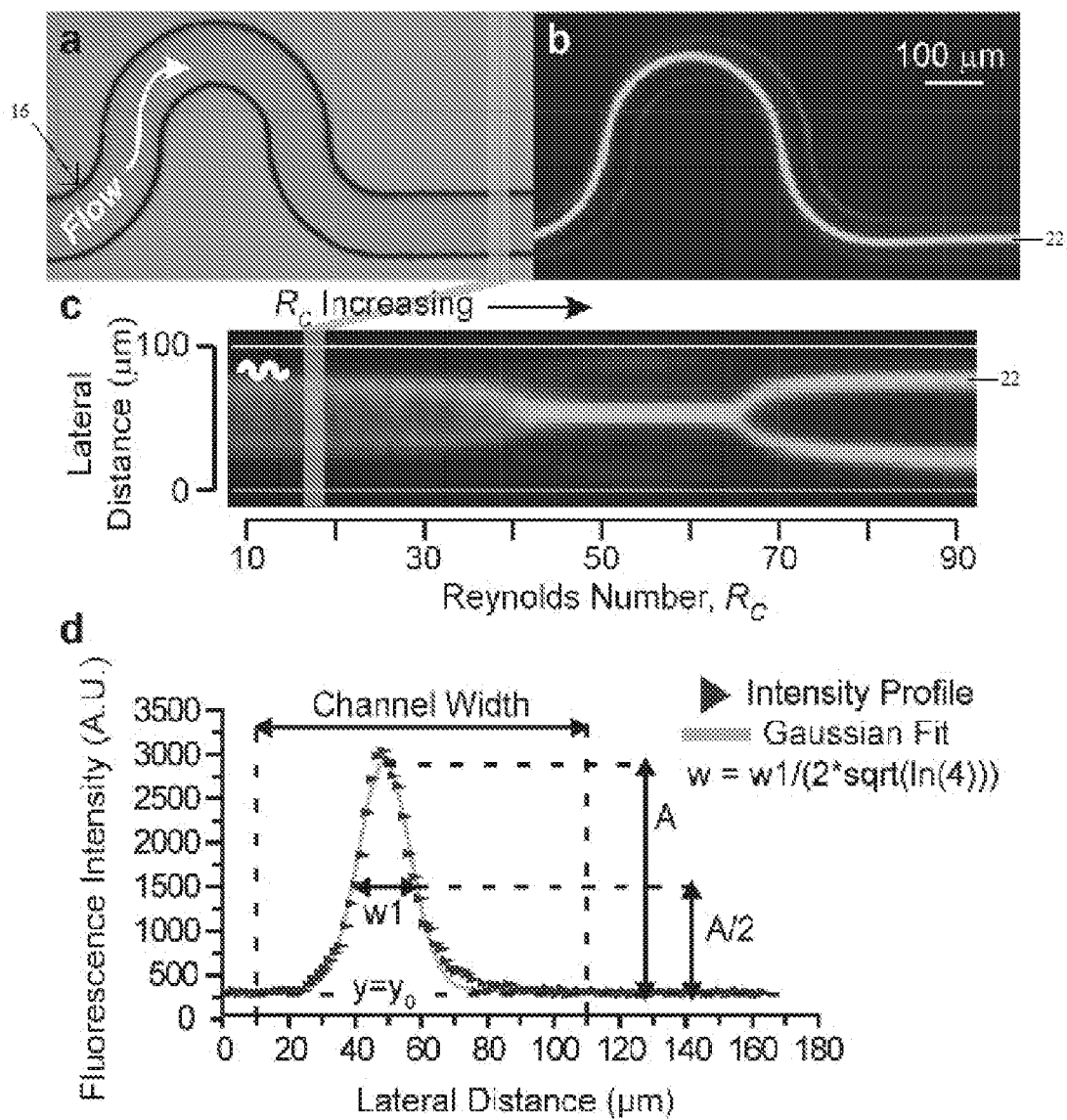
Figs. 6a-d

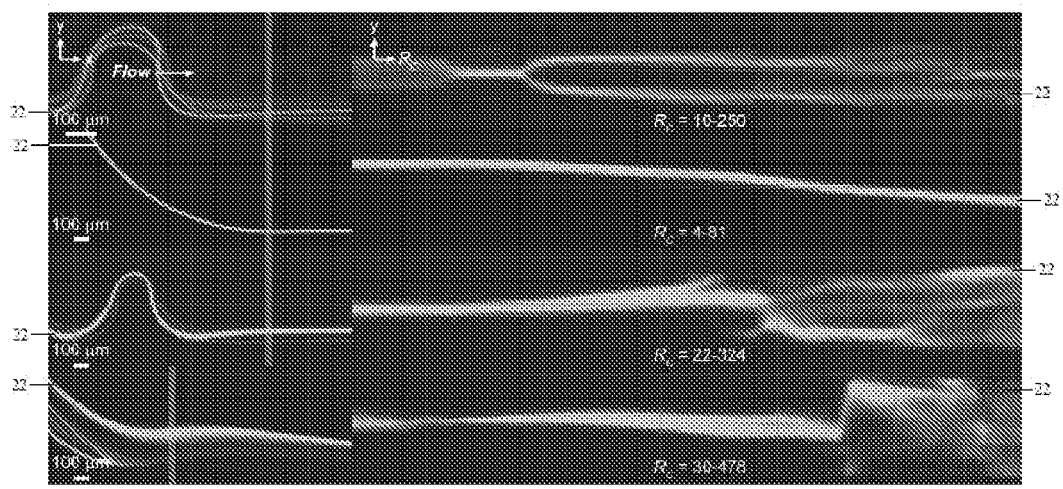
Fig. 7
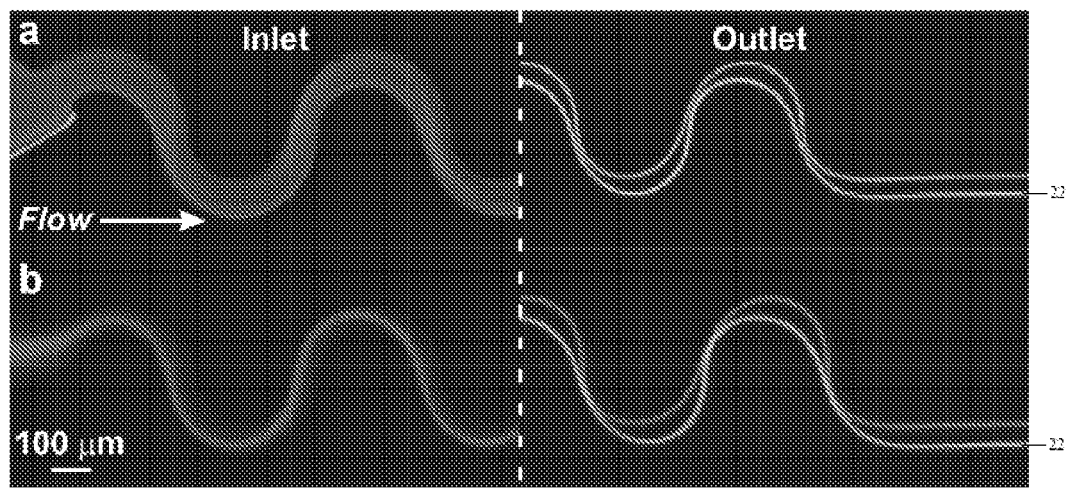
Figs. 8a-b

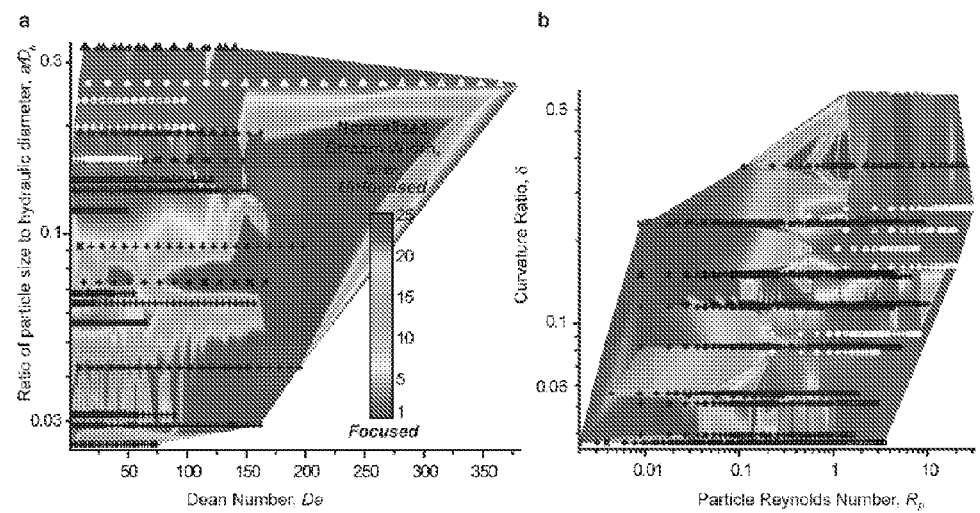
Figs. 9a-b
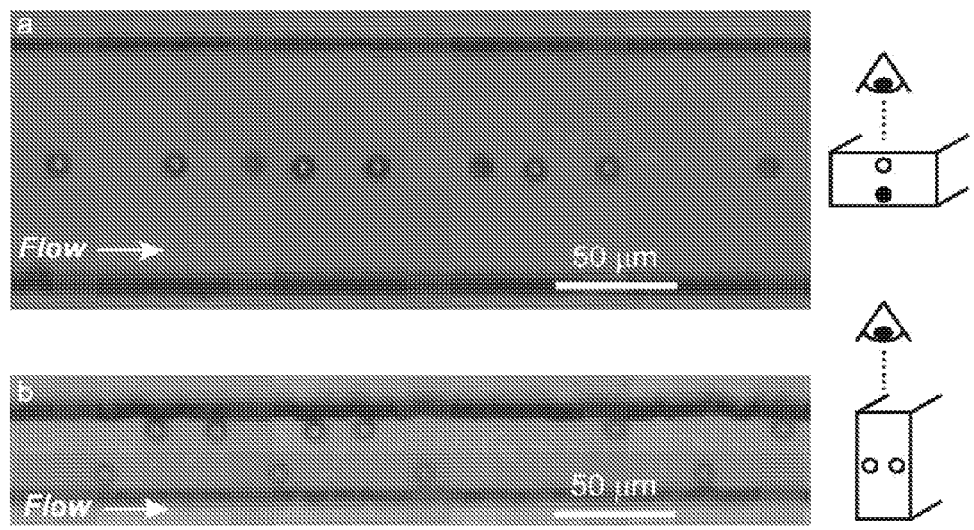
Figs. 10a-b

INERTIAL PARTICLE FOCUSING SYSTEM

RELATED APPLICATION

This application claims priority to U.S. Provisional Patent Application No. 61/382,300 filed on Sep. 13, 2010. Priority is claimed pursuant to 35 U.S.C. §119. The above-noted patent application is incorporated by reference as if set forth fully herein.

FIELD OF THE INVENTION

The field of the invention generally relates to systems used to focus, separate and sort particles or cells. More particularly, the invention relates to microfluidic-based systems that focus, separate and/or sort biological materials (e.g., cells or cellular components) or particles.

BACKGROUND

Microfluidic-based systems are becoming widely used in biological and chemical analysis applications. Traditionally, flow cytometry focuses cells or particles, i.e., organize them into one or more stream lines. Typically, the stream lines are single file lines of cells or particles. For example, in conventional flow cytometry, a mixture or cells or particles in a carrier fluid is hydrodynamically focused using a sheath fluid to align cells or particles in one or more ordered streams. This active focusing requires that the practitioner manipulate the sample and control the flow conditions for the sheath fluid. It also requires vast reservoirs for sterile sheath fluid, complicating miniaturization of flow cytometers for point-of-care diagnostics.

After the cells or particles are focused into ordered streams, they can be counted. Alternatively, the cells or particles, which may be labeled with a fluorescent label or the like, could be interrogated using, for example, a laser or other optical apparatus to identify particular cells or particles of interest within the streams. After encapsulation in a droplet, the cells or particles of interest can then be deflected downstream of the interrogation region into an appropriate collection chamber or the like by using high-voltage electrical plates. For example, the cell or particle contained within the droplet of carrier fluid may be positively or negatively charged which can then be attracted (or repulsed) by the charged electrical plates. This causes movement of the droplets into the proper collection chamber for sorting after focusing.

Recently, various passive focusing systems and methods have been proposed for focusing cells or particles without a sheath fluid. See U.S. Patent App. Pub. No. 2009/0014360 to Toner et al. ("Toner et al."), which is incorporated by reference herein. Toner et al. describes ordering of particles suspended in a fluid traveling through a microfluidic channel. The carrier fluid, the channel, and the pumping element are configured to cause inertial forces to act on and focus the cells and particles.

Fluid inertia is usually not considered important in microfluidic systems as the Reynolds number, the ratio of inertial to viscous forces is small, such that particles suspended in microfluidic flows have been expected to follow fluid streamlines (i.e., viscous forces dominate). Very recently, these inertial lift forces have also been shown to be extremely useful in microfluidic systems for a number of particle manipulation applications including focusing, ordering, separation, filtration, segregation, and extraction. For applications including focusing and separation, multiple geometries have been explored including straight channels, spirals, and asymmetrically curved turns. There is little and conflicting understanding of the underlying physical forces governing these systems and how to best design systems for separating arbitrary-sized particles at desired high rates. This understanding would enable practical high-throughput cell focusing, blood filtration, and water treatment in a cost-effective filterless platform.

Particle focusing in curved channels has been explained as a balance of lift forces from the wall, centrifugal forces, Saffman and Magnus forces, and Dean vortex flow. The Saffman and Magnus forces, in particular, require the assumption that particles lead or lag flow. Others contend particles are mostly entrained in flow, the result of a balance of inertial lift forces and entrainment in Dean flow. The relation between the Dean number and the Dean velocity has also been defined differently. Another area of incomplete understanding involves the inertial lift force. Some rely on derivations of the inertial lift force, which use a point-particle assumption, contrary to recent results suggesting a finite particle size assumption provides a more accurate description.

Inertial lift forces have been identified as one of the underlying players in focusing of particles of diameter, a, in channels of hydraulic diameter, $D_h$, at finite channel Reynolds numbers, $R_C = \rho U D_h / \mu$. Here $\rho$ is the fluid density, $\mu$ is the fluid viscosity, and U is the mean channel velocity. Using point-particle assumptions the lift force leading to lateral migration and focusing was found to scale uniformly throughout the channel ($F_L = f_L \rho U^2 a^4 / D_h^2$, where $f_L$ may be regarded as a lift coefficient dependent on the particle's position in the channel, the channel Reynolds number, and the aspect ratio of the channel). There appears to be a finite-particle size effect that leads to a more complex dependence of lift force on channel position and particle size: ($F_L = f_1 \rho U^2 a^3 / D_h$ near the channel centerline and $F_L = f_2 \rho U^2 a^6 / D_h^4$ near the wall). Assuming the near centerline scaling leads to slower lateral particle migration than near the channel wall, the lateral migration distance for a given downstream distance can be shown to be proportional to a particle Reynolds number, $R_p$ ($R_p = \rho U a^2 / \mu D_h$).

In curved channel geometries non-intuitive lateral particle migration is observed. Secondary flows due to centrifugal effects on the fluid, i.e. Dean flow, have been postulated to act on particles and affect equilibrium positions but have not been systematically observed. Secondary flows capable of segregating suspended microparticles can also be generated by microstructured channels and leading to particle localization even at very high particle volume fractions. Dean flow is characterized by counter-rotating vortices such that flow at the midline of a channel cross-section is directed outward around a turn and, satisfying conservation of mass, slower moving fluid at the top and bottom of the channel is directed inward. Two dimensionless groups prescribe the flow in these channels of radius of curvature, r, the Dean number, De ($De = R_C (D_h/2r)^{1/2}$), and the curvature ratio, $\delta$ ($\delta = D_h/2r$). Dean flow, scaling with $De^2$ leads to a drag force upon particles lagging the secondary flow and directed in its direction. The maximum value of this force can be estimated by Stokes drag ($F_D \sim \rho U^2 a D_h^2 r^{-1}$).

The current understanding of focusing in curved channel systems is based on previous work with asymmetrically curved channels and suggests a balance between inertial lift and entrainment by secondary vortices. There is a need for identification of important geometric factors of the microchannels that allow for further increases in throughput or focusing of potentially arbitrary particle sizes. There is also a need for inertial particle focusing systems configured for passive focusing at higher Reynolds numbers and throughputs. Further, there is a need for methods of designing microchannels for such systems that increase passive focus throughput for cells and particles of a known size.

SUMMARY

In one embodiment, a method of manufacturing an inertial particle focusing system for use with a particle having diameter (a) includes forming a curved microchannel into a substrate, said microchannel having a radius of curvature (r), and a channel hydraulic diameter ($D_h$), wherein the ratio of r to $D_h$ satisfies the following criterion: $2ra^2/D_h^3 \geq 0.037$. The method may also include selecting an r and calculating $D_h$ according to the following formula:

$$D_h \leq \sqrt[3]{\frac{2ra^2}{0.037}}.$$

r may be selected from the range between 50 µm and 5 mm. Alternatively, the method may also include selecting a $D_h$ and calculating r according to the following formula: $r > 0.037 \times D_h^3/2a^2$. $D_h$ may be selected from the range between 10 µm and 1 mm.

The method may also include replica molding, i.e., forming a polymer on silicon mold defining a curved microchannel using a first polymer, wherein the ratio of r to $D_h$ satisfies the criterion, producing a polymer chip from the mold using a second polymer, forming inlet and outlet holes in the chip, and bonding the chip to glass. The first polymer may be a photoresist, such as SU-8 50™. The second polymer may be poly-dimethylsiloxane, thermoset polyester, polyurethane methacrylate, Norland™ optical adhesive, etc. The method may include forming a microchannel with a plurality of curves. Other manufacturing methods include hot embossing, injection molding, laser ablation, and etching and bonding of silicon or glass.

In another embodiment, an inertial particle focusing system for use with a particle having diameter (a) includes a curved microchannel disposed in a substrate, said microchannel having a radius of curvature (r), and a channel hydraulic diameter ($D_h$), wherein the ratio of r to $D_h$ satisfies the following criterion: $2ra^2/D_h^3 \geq 0.037$. The microchannel may also include an inlet, a filter region, a curved region, a straight region, and an outlet. The curved region may include a plurality of curves. Also, the microchannel may have a rectangular or square cross-section. The curved microchannel may include an upstream curve and a downstream curve, wherein the upstream and downstream curves have different radii of curvature. In some embodiments, one of the upstream curve and the downstream curve has a smaller radius and the other has a larger radius, such that a ratio of the larger radius to the smaller radius is greater than 6. The upstream radius of curvature may be smaller than the downstream radius of curvature.

In yet another embodiment, a method of focusing particles of diameter a includes flowing a population of particles within a inertial particle focusing system including a curved microchannel disposed in a substrate, said microchannel having a radius of curvature (r), and a channel hydraulic diameter ($D_h$), wherein the ratio of r to $D_h$ satisfies the following criterion: $2ra^2/D_h^3 \geq 0.037$. The method may include flowing the particles at a channel Reynolds numbers up to $R_C=270$. Alternatively, the method may include flowing the particles at throughputs up to approximately 41,000 particles/s.

BRIEF DESCRIPTION OF THE DRAWINGS

FIG. 1a is a cross-sectional schematic view of a microchannel with a single turn, in which particles move in the direction of secondary flow.

FIG. 1b is a top schematic view of a microchannel with a single turn, in which particles migrate laterally across the channel.

FIG. 1c is a series of three fluorescent streak images of particles in single turns at three flow rates.

FIG. 1d is a series of two high speed images of particles migrating during flow through a microchannel.

FIG. 1e is a plot of lateral particle migration velocity ($U_p$) against mean flow velocity (U) and fits a quadratic function to the data points.

FIG. 2a is a series of two fluorescent streak images of fluorescent particles flowing in rectangular microchannels.

FIG. 2b is a series of two fluorescence intensity profiles across the microchannels in FIG. 2a.

FIG. 3a is a series of three fluorescent streak images of particles in straight microchannels.

FIG. 3b is a series of three fluorescent streak images of particles in curved microchannels.

FIG. 3c graph of the width of the particle streak normalized against the diameter of a single particle against the distance the particles traveled in straight and curved channels at high and low channel Reynolds numbers, $R_C$.

FIG. 4a is a schematic view of a inertial particle focusing system according to one embodiment of the invention.

FIG. 4b is a perspective view of two adjacent turns of an asymmetrically curved microchannel according to another embodiment of the invention.

FIG. 4c is an axial cross-sectional view of an asymmetrically curved microchannel according to another embodiment of the invention.

FIG. 4d is a series of four Reynolds number—space maps for channels with two turns with the same hydraulic diameter, $D_h$, but a varied r.

FIG. 4e in a series of three Reynolds number—space maps for channels with two turns where both $D_h$ and r are varied.

FIG. 5a is a state diagram for particle focusing in curved channels as a function of the dimensionless groups $R_f$ and $R_C$.

FIG. 5b is a series of three Reynolds number—space maps of fluorescent streak images.

FIG. 6a is a light micrograph of the end of the curved region of a microchannel.

FIG. 6b is a fluorescent streak image of flowing fluorescent polystyrene beads in the same region of the microchannel of FIG. 6a.

FIG. 6c is a Reynolds number—space maps for channels with two turns.

FIG. 6d is a graph of fluorescence intensity against lateral distance from the inner (lower) wall of the channel, wherein a Gaussian function has been fitted to the data.

FIG. 7 is a series of four fluorescent streak images and a series of four Reynolds number—space maps.

FIGS. 8a-b are two pairs of fluorescent streak images; the first of each pair is taken at a microchannel inlet and the second at the respective outlet.

FIGS. 9a-b are state diagrams for particle focusing in curved channels as a function of various dimensionless groups.

FIGS. 10a-b are light micrographs of high aspect ratio channels (where the one dimension of the cross-section is larger than the other) from two angles: (a) along the short axis of the cross-section; and (b) along the long axis of the cross-section.

DETAILED DESCRIPTION OF THE ILLUSTRATED EMBODIMENTS

Modification of Particle Equilibrium Positions in Curved Channels

FIGS. 1a-e show lateral particle migration in a single turn. The term "particle," as used in this application, encompasses, but is not limited to, cells, bio-particles, emulsions, and polymeric and metal particles. FIG. 1a is a cross-sectional schematic view of a microchannel 16 with a single turn, in which particles 10a, 10b, 10c, 12a, 12b, 12c move in the direction of secondary flow. FIG. 1b is a top schematic view of a microchannel 16 with a single turn 14, in which particles migrate laterally across the channel 16. FIG. 1c is a series of three fluorescent streak images of particles in single turns 16 at three flow rates, which show the schematically shown behavior in FIGS. 1a and 1b. The channels 16 are 30 µm wide and 54 µm tall. FIG. 1d is a series of two high speed images in which a particle aligned at the inside wall 20 before the turn 14 migrates laterally across the channel remaining in one focal plane, while a particle at the outer wall 28 moves out of focus while migrating inward. FIG. 1e plots lateral particle migration velocity, ($U_p$) against mean flow velocity (U) and fits a quadratic function to the data points.

FIGS. 1a-e show transverse motion of aligned incoming particle streams 10, 12 around a single turn 14 of a curved channel 16 of constant radius of curvature (r). The input to the channel 16 includes two well-focused particle streams, an inner particle stream 10, and an outer particle stream 12. The streams 10, 12 are formed in a straight rectangular channels (not shown) using inertial migration. In rectangular channels, particles tend to migrate to two equilibrium positions 10a, 12a along the short axis bisecting the long axis of the rectangular cross-section of the channel. See FIG. 1a.

FIG. 1a is a schematic axial cross-section view showing the secondary Dean flow in a curved channel 16 containing particles 10a, 10b, 10c, 12a, 12b, 12c flowing in a carrier fluid 18. Through the turn 14, particles 10a, 10b, 10c, 12a, 12b, 12c migrate in paths corresponding to that of the secondary Dean flow in these systems (i.e., counter-rotating vortices where flow at the short axis bisecting the long axis of the rectangular cross-section is directed to the outside of the turn 14 and flow at the top and bottom of the channel cross section is directed inward).

FIG. 1b is a schematic longitudinal cross-section view showing particle streams resulting from the secondary Dean flow at a sufficiently high De. FIG. 1b also indicates the distance ($x_1$ to $x_4$) the inner particle stream 10 moves away from the inner wall 20 of the curved channel 14. Further, FIG. 1b indicates the mean flow (downstream) velocity U and the particle migration velocity (perpendicular to the primary flow direction $U_p$) acting on particles in the inner particle stream 10.

At sufficiently high De (e.g., at De=43), fluorescent streak images of focused particles in FIG. 1c verify that particles from the inner particle stream 10a flow outward 10c and particles from the outer particle stream 12a flow inward 12c. For higher De the inner particle stream 10 migrates outward through the turn 14 in the channel 16, while the outer particle stream 12 migrates inward presumably over the top or bottom of the channel midplane. This inward migration is contrary to any dominant centrifugal effect on the particles 12a, 12b, 12c themselves.

High speed microscopic image in FIG. 1d confirm that particles 10a starting in the inner particle stream 10 follow a uniform path across the channel 16 at one z-plane and focal length. On the other hand, particles 12a in the outer particle stream 12 begin at a single z-plane then change focus as they move inward and upward, before returning to the original z-plane at the inner channel wall 20. These images are consistent with FIG. 1a and show that Dean flow modifies inertial lift equilibrium positions.

In the absence of dominant inertial lift forces we would expect lateral particle migration velocity scales with $De^2$ ($U_D \sim De^2 v/D_h$) or the average downstream velocity squared ($U^2$) for a channel of constant curvature. FIG. 1e plots the particle migration velocity (perpendicular to the primary flow direction $U_p$) against the mean flow (downstream) velocity U. FIG. 1e shows the particle migration perpendicular to the primary flow direction ($U_p$) for particles beginning in both inner and outer particle streams 10, 12 as they moved across the channel 16. For particles in the inner stream 10 $U_p=0.036U^2$ ($R^2=0.99$) while for particles in the outer stream 12 $U_p=0.13(U-1.34)^2$ ($R^2=0.94$). In FIG. 1e, the parabolic fit for the outer stream 12 is shifted to intersect zero at a higher mean channel velocity as at lower velocities (<~1.3 m/s) particles are observed to migrate vertically only (i.e. $U_p=0$). Above U~1.3 m/s particles are able to travel far enough vertically to follow the secondary flow that is directed across the channel 16.

There is also an asymmetry in the system such that the drag on particles 12a directed vertically and inward around a turn is significantly less than the drag on particles 10a directed outward around the turn. The quadratic behavior of particle velocity scaling demonstrates the critical effect of Dean flow on perturbing inertial focusing equilibrium positions. Lift forces, which act on the particles flowing through a curved channel, must be accounted for in analyses of particle velocity data.

For a particle 10a (see FIG. 1a) initially focused to the inner stream 10 when the Dean number is low, the particle motion outward will be reduced by an inward directed lift force as long as the particle does not cross the vertical midline of the channel. Thus, the measured $U_p$ will be reduced by the shear gradient lift force in this case. If the Dean number is sufficiently large to cause the particle to cross the channel midline, balanced lift directed inward (before crossing the midline) and outward (after crossing the midline) leads to less of an effect on the measured $U_p$.

FIGS. 2a-b demonstrate curved channels 16 concentrating particles by directing their lateral migration to more stable equilibrium positions. FIG. 2a is a series of two fluorescent streak images of 9.9 µm fluorescent particles flowing in rectangular (100 µm wide by 50 µm tall) microchannels, which show particle densities shifting to stable mid-stream 24 equilibrium positions after a single turn 14. FIG. 2b is a series of two fluorescence intensity profiles across the channel 16, which show the density of particles in the center stream 24 increasing after a single turn 14 while the side streams 26 exhibit a corresponding decrease in density.

Secondary flows in curved channels also selectively perturb equilibrium positions that are stable in straight channels and reduce focusing to a smaller subset of equilibrium positions that are stable in the presence of the superposed secondary flow. In a rectangular cross-section microchannel with width 100 µm and height 54 µm, 9.9 µm particles focused to four equilibrium positions (not shown). In such a microchannel, $a/D_h$ is lower than in the embodiment in FIGS. 1a-e thus additional equilibrium positions are occupied. After a single turn most particles are focused to two positions on the top and bottom faces of the channel 16. In FIG. 2a, these two positions appear as one streak 22 from above.

FIG. 2b plots the fluorescence intensity against the distance from the inner wall 20 of a channel 16. The intensity profiles of fluorescence streak images show that the density of particles in the center streams 24 increased with a corresponding decrease in particle density in the side streams 26. The center streams 24 are focused near the center of one of the Dean vortices and are not appreciably deflected from their inertial equilibrium positions by the rotational flow. Particles near the side streams 26 (focusing positions) are significantly deflected and spiral into the stable center streams 24 (focusing positions). This mechanism reduces symmetry for inertial focusing in curved microchannels 16 for practical applications. The center streams 24 are closer to the center of the channel 16 at a higher Dean number. Particles may have shifted closer to the top and bottom walls in the z-plane at higher Reynolds number such that the balance between lift and Dean flow may be different.

FIGS. 3a-c show particles migrating faster to geometrically determined equilibrium positions in curved microchannels. FIG. 3a is a series of three fluorescent streak images of particles in 100×50 μm straight microchannels 16, showing that the particles migrate to well-defined single streak 22 (focusing positions) downstream (flow rate equals 6.7 μL/s). FIG. 3b is a series of three fluorescent streak images of particles in 100×50 μm curved microchannels with small radius of curvature equal to 350 μm, and large radius of curvature equal to 950 μm, showing that the particles migrate to well-defined focusing positions in less than six turns (flow rate equals 6.7 μL/s). FIG. 3c plots the width of the particle streak 22 normalized against the diameter of a single particle against the distance the particles traveled in straight and curved channels at high (89) and low (22) channel Reynolds numbers, $R_C$. These images show that, when Dean number, De is sufficiently high, curved channels focus particles in a much shorter distance than straight channels.

Because curved microchannels 16 easily perturb flowing particles from unstable positions they can be used to enhance the speed of lateral particle migration to stable equilibrium positions. That is, at a sufficient De curved channels 16 will cause faster focusing to predicted equilibrium positions than straight channels 16. In a straight channel 16 of width larger than height (FIG. 10a) focusing to a single streak 22 is observed after about 4 cm, as shown in FIG. 3a. In a repeating curved channel with the same aspect ratio highly focused streaks 22 are reached within the first six turns in less than about 1 cm (FIG. 3b).

This effect requires appreciable secondary flow in the curved channels 16. When the $R_C$ or De is low (22 or 4, respectively) the two channels focus particles at approximately the same downstream length, as shown in FIG. 3c. When either $R_C$ or De is increased to 89 or 17, respectively, curved channels 16 induce focusing (manifested by smaller stream width) in a shorter distance, as shown in FIG. 3c. Shorter focusing distance results in decreased fluidic resistance and thus pressure and power required to drive the flow. In fact, it appears that for optimized geometries shown later, fluidic resistance is the limiting factor for increasing the throughput of focusing, since high pressure leads to leakage at fluid inlets.

Controlling Focusing at High Reynolds Numbers.

Secondary flow in curved channels is the dominant factor contributing to modified equilibrium positions for particles flowing at finite Reynolds numbers. This secondary flow interacts with the underlying equilibrium positions due to inertial migration in a highly complex manner. Quantitating this interplay allows for controlled high-throughput particle focusing and separation of arbitrary-sized particles.

Inertial lift forces ($F_L$) and drag forces due to the secondary flow ($F_D$) act in superposition, such that modification of inertial lift equilibrium positions can be thought of as a problem of the relative magnitude of these two forces at each spatial position within the channel cross-section. As modified using scaling of inertial lift for finite size particles, an "inertial force ratio," $R_f = F_L/F_D = ra^2/D_h^3 f(R_C, x/w, y/h, h/w)$, can be defined, where f is a dimensionless function that contains the dependency of the two forces on particle location, channel Reynolds number, and channel aspect ratio. This ratio is useful as a simple parameter to characterize whether particles would: (i) ($F_L/F_D \ll 1$) become entirely entrained in the secondary flow, (ii) ($F_L/F_D \gg 1$) remain unaffected by the secondary flow, or (iii) ($F_L/F_D \sim 1$) reach modified equilibrium positions from the superposition of the two effects.

A previous definition of $R_f$ was based on point-particle assumptions and a full dependence on f. The observation that particles do not focus near the wall suggests that shear gradient lift, not wall effect lift, balances Dean drag. Accordingly, an improved scaling of the inertial lift force calculated for particles far from the wall defines $R_f = 2ra^2/D_h^3$. By maintaining a constant channel aspect ratio (and neglecting the complexity off) and because the inertial lift coefficient is only weakly dependent on $R_C$, $R_f$ becomes the dominant dimensionless group controlling focusing behavior in the three (i-iii) regimes. f ranges from 0.02 to 0.03 for channel Reynolds number from 20-95.

The omission of the complex f and $R_C$ dependence makes $R_f$ an average for the channel and more accessible as a design parameter. For instance, for a set of known $R_f$, r, and a, $D_h$ can be calculated. Also, for a set of known $R_f$, a, and $D_h$, r can be calculated.

FIGS. 4a-e show curved channels and focusing maps therein. In FIG. 4a, microparticles are pumped by a syringe pump (not shown) through tubing 30 into the device's inlet 32, through a filter 34, forty turns 14, and collected at the outlet 36. FIG. 4b illustrates curved channels 16 consisting of two turns with varying radii of curvature, $r_1$ & $r_2$, measured from the center 38 of the channel 16 to the apex 40 of the turn 14. FIG. 4c shows the height, h, and width, w, of the channel 16, which are defined by the channel's 16 cross-section at the apex 40 of the turn 14. FIG. 4d is a series of four Reynolds number—space maps for channels with two turns 14 with the same hydraulic diameter, $D_h$, but a varied r. A decrease in particle streak 22 bifurcation symmetry, an increase in bifurcation $R_C$, and an increase in stability of focused streaks 22 over a large range of $R_C$ are apparent from FIG. 4d. These channels 16 have uniform widths of 100 μm and heights of 50 μm. FIG. 4e in a series of three Reynolds number—space maps for channels with two turns where both $D_h$ and r are varied. When both $D_h$ and r are adjusted so that the scaling of the ratio of inertial lift force, $F_L$, to Dean drag force, $F_D$, is high (bottom map) there is a high degree of focusing over a larger range of $R_C$. These channels 16 are imaged after the curving region where the width has been reduced to 100 μm for consistency. However, the width varies throughout the curving region ($\cong$100 mm). The height is 50 μm.

FIGS. 4a-e demonstrate that the greater the asymmetry of the radii of curvature, $r_1$ & $r_2$, the greater the range of flow rates or Reynolds numbers, $R_C$, at which focusing could be achieved. A ratio of large to small radius ($r_2/r_1$) greater than 6 should be considered.

The complexity of the spatial and Reynolds number dependence of both inertial lift forces and the secondary flow results in rich modes of focusing behavior in curved channel systems with repeating curvature (FIGS. 4 and 7). The most complex behavior was observed in symmetric curving channels (FIG. 7). When the focusing streak bifurcates, the density of particle positions downstream is dependent on initial conditions (FIG. 8).

$R_C$—space maps created by assembling slices of streak images for increasing Reynolds numbers (FIGS. 6a-c) visualize the complexity of focusing over a range of Reynolds numbers. These maps show trends in focusing behavior for symmetric and asymmetric curving channels with various hydraulic diameters, $D_h$, curvature, r, and asymmetry (FIG. 4). FIG. 4d illustrates several effects that change with channel symmetry (symmetric—asymmetric). (1) Focusing to a single streak (containing particles located at two z-heights) occurs at lower $R_C$ as asymmetry increases. (2) The symmetric bifurcation of the focused streak that occurs at $R_C$~70 is pushed to higher $R_C$ with increased asymmetry, and (3) the bifurcation itself becomes more asymmetric with particles preferring the streak corresponding to the larger radius turn. FIG. 4e shows that increasing the radius of curvature while decreasing the hydraulic diameter (to increase $R_f$) improved single streak focusing.

FIGS. 5a-b show that the ratio of forces in the secondary flow direction is a critical factor affecting the degree of focusing. FIG. 5a is a state diagram for particle focusing in curved channels 16 as a function of the dimensionless groups $R_f$ and $R_C$. Data points for three sizes of particles are indicated by black shapes. (●) indicates conditions where a single streak 22 of particles less than twice the diameter of a particle was attained. (▲) indicates multiples streaks 22 of which one is less than twice the diameter of a particle. (+) indicates concentration of particles to streaks 22 greater than twice the diameter of a particle. (X) indicates no lateral particle migration. White symbols indicate the focus results using channels 16 designed to focus 2.2 μm particles with guidance from the original state diagram.

According to the bar on the right side of FIG. 5a, a stream width of 25 correlates with unfocused flow and a stream width of 1 correlates with focused flow. FIG. 5b is a series of three Reynolds number—space maps of fluorescent streak 22 images show how focusing evolves for three particle sizes in relation to the state diagram.

The inertial force ratio, $R_f$, has a quantifiable effect on particle focusing behavior. Adjustable parameters for curved channel focusing systems include channel geometry and particle sizes. Channel schematic and geometric definitions are shown in FIGS. 4a-c. The state diagram in FIG. 5a shows focusing accuracy as a function of $R_C$ and $R_f$. The z-axis (focusing accuracy) corresponds to the width of a Gaussian function fit to the intensity profile of a focused streak normalized by the diameter of a single particle (see FIG. 6d for analysis method). Points where the width of either a single particle streak or a distinguishable streak among multiple focused streaks is less than twice the diameter of a single particle are designated with (●) and (▲), respectively. Points where particles are concentrated to a streamline larger than twice the diameter of the particle or no migration was observed are designated with (+) and (X), respectively. At $R_f$ below a threshold level ($R_f$~0.037), particles either concentrated to a streamline larger than twice the diameter of the particle (+) or did not migrate (X). Quantifying equilibrium position stability across a large range of Reynolds numbers results in a state diagram (FIG. 5c) for the balance of inertial lift and entrainment by secondary vortices, and expand focusing to an order of magnitude higher Reynolds numbers and throughputs ($R_C$=270, ~41,000 particles/s).

In addition to the role of $R_f$ in particle focusing behavior, a sufficiently large $R_P$, another dimensionless parameter, is also important in particle focusing (FIG. 9). The quotient $a/D_h$ has been validated as a channel design parameter. This quotient is still useful to predict focusing behavior in these systems and is incorporated into $R_f$. However, curvature introduces complex focusing behavior which is better predicted in a single parameter, like $R_f$, that accounts for the complete channel geometry, including channel curvature.

FIG. 5a also shows that the threshold level ($R_f$~0.037) can be used to design curved channels 16 that focus particles of a different known size. Microchannels 16 were designed for which $R_f$ would be greater than 0.037 for 2.2 μm particles. Those microchannels were then used to focus the 2.2 μm particles. The focusing results are recorded as white symbols in the FIG. 5a state figure and in the FIG. 5b $R_C$—space map. Those results show that using the threshold level of $R_f$~0.037 accurately determines the channel geometry for focusing particles of a known size.

The state diagram in FIG. 5a, along with those in FIGS. 9a-b are described in detail in *Particle focusing mechanisms in curving confined flows*, Gossett, D. R. and Di Carlo, D., *Anal. Chem.*, 2009, 81(20), 8,459-8,465 and the supporting information therefore, which are both incorporated by reference.

The design parameter $R_f$>0.037 results in channels able to focus particles to narrow streaks equal to the diameter of the particle at a Channel Reynolds number of 270 in a channel that has a varying width greater than 100 μm and a height of 50 μm. This Channel Reynolds number is several orders of magnitude higher than most current microfluidic focusing systems with a single inlet channel and no externally applied forces.

As shown in FIG. 4a, inertial particle focusing systems for use with a particle having diameter (a) can be made with a curved microchannel in a substrate, said microchannel having a radius of curvature (r), and a channel hydraulic diameter ($D_h$), wherein the ratio of r to $D_h$ satisfies the following criterion: $2ra^2/D_h^3 \geq 0.037$. The microchannel may also include an inlet 32, a filter region 34, a curved region, a straight region, and an outlet 36. The curved region may include a plurality of curves. Also, the microchannel may have a rectangular cross-section. The curved microchannel may include an upstream curve and a downstream curve, wherein the upstream and downstream curves have different radii of curvature. The upstream radius of curvature may be smaller than the downstream radius of curvature.

FIGS. 6a-d depict quantification of particle focusing. FIG. 6a is a light micrograph of the end of the curved region of a 100 μm wide microchannel 16. FIG. 6b is a fluorescent streak 22 image (1 s exposure time) of flowing fluorescent polystyrene beads (9.9 μm diameter) in the same region of the microchannel of FIG. 6a, depicting geometrically determined focusing positions. In FIG. 6c, fluorescent images are recorded across a range of Reynolds numbers increased at fixed intervals. Vertical slices of these images are assembled such that the horizontal axis is the channel Reynolds number. In FIG. 6d, a Gaussian function is fit to vertical intensity profiles taken across the channel 16. The streak width corresponds to the width at half the amplitude of the function. Similar plots can be obtained for single particles to allow for normalization of focusing accuracy.

FIG. 7 is a series of four fluorescent streak 22 images and a series of four Reynolds number—space maps (assembled fluorescent images; see FIG. 6c). The fluorescent streak 22 images show equilibrium positions becoming increasingly complex at high Reynolds number. The Reynolds number—space maps show the complex evolution of focused streaks 22 as $R_C$ increases, especially as channel asymmetry decreases.

FIGS. 8a-b depict two pairs of fluorescent streak 22 images; the first of each pair is taken at a microchannel inlet and the second at the respective outlet. These images show that inlet particle distribution affects outlet distribution. FIG. 8a shows that after randomly distributed particles are flowed through a symmetrically curved channel, the outlet particles occupy two equilibrium positions at equal density. FIG. 8b shows that when the inlet distribution is made non-uniform, particles migrate to proximal equilibrium positions, which may result in differing concentrations in the symmetric focusing positions.

FIGS. 9a-b are state diagrams for particle focusing in curved channels 16 as a function of various dimensionless groups. FIG. 9a plots the accuracy of focusing (z-axis) for the ratio of particle size to hydraulic diameter versus Dean number. FIG. 9b plots the accuracy of focusing (z-axis) for the ratio of curvature versus particle Reynolds number. The layout of these state diagrams and symbols used therein are similar to those in FIG. 5a above.

FIGS. 10a-b are light micrographs of high aspect ratio channels (where the one dimension of the cross-section is larger than the other) from two angles: (a) along the short axis of the cross-section; and (b) along the long axis of the cross-section. FIG. 10a shows that when observing a high aspect ratio channel where the width is larger than the height, particles focus to two focal planes centered on the channel long face. FIG. 10b shows that when observing a high aspect ratio channel where the height is larger than the width, particles appear in the same focal plane opposite one another at the midline.

Microfabrication.

Microfluidic devices were fabricated using a standard poly-dimethylsiloxane replica molding process as described in *Equilibrium separation and filtration of particles using differential inertial focusing*, Di Carlo, D.; Edd, J. F.; Irimia, D.; Tompkins, R. G.; Toner, M., *Analytical Chemistry* 2008, 80 (6), 2204-2211, which is incorporated herein by reference. Briefly, standard lithographic techniques were used to produce a SU-8 50™ (MicroChem Corp.) on silicon mold. PDMS chips were produced from this mold using Sylgard 184™ Elastomer Kit (Dow Corning Corporation). Inlet and outlet holes were punched through PDMS using a coated round punch from Technical Innovations, Inc. PDMS and glass were activated by air plasma and bonded together to form channels.

Microfluidic Channel Designs.

The variables considered in designing microfluidic channels were hydraulic diameter, radius of curvature, and aspect ratio. The microchannels can have a single-turn or multiple-turns with systematically varied geometries. Channel may contain an inlet, a filter region, 40 turns (in the case of multiple-turn microchannels), a straight region for imaging, and an outlet. The inlet and outlet were large enough to fit tubing for the injection of particle suspensions. The filter region contained large rectangular posts closely spaced to trap dust particles and aggregates. The turns were followed by a short straight or trapezoidal region where the channel width was adjusted to 100 μm then a straight region leading to an outlet.

Particle Suspensions.

Internally dyed green fluorescent polystyrene microspheres were purchased from Thermo Scientific. 9.9-μm (Product #G1000), 4.8-μm (Product #G0500), 2.2-μm (Product #G0100) and were diluted to 0.1% (weight/weight) with deionized water with 0.1% Tween 80 (Fisher Chemical Product #T164). For non-uniform inlet conditions, particles were suspended in a more dense solution of 10% (wt/vol) Potassium Iodide such that particles "settled" to the top of our tubing and entered the microchannels from a narrow location.

Microparticle suspensions were pumped through the devices by a Harvard Apparatus PHD 2000™ Syringe Pump. The loaded syringe was connected to 1/32×0.02" PEEK tubing (Upchurch Scientific Product #1569) by a ½" luer stub (Instech Solomon Product #LS25) and tubing was secured in the punched hole.

Fluorescence Imaging.

Fluorescent images were recorded using a Photometrics CoolSNAP HQ²™ CCD camera mounted on a Nikon Eclipse Ti™ microscope. Images were captured with Nikon NIS-Elements AR 3.0™ software. In the characterization of the original devices, for 2.2, 4.8, and 9.9 μm fluorescent microparticles exposure times of 5, 2, and 1 s, respectively, were used. Particle suspensions were pumped through the microchannels at an initial flow rate of 50 μL/min. The flow rate was increased by 50 μL/min every 10 s. Vertical slices from ND2 acquired videos were assembled using the Nikon software. (FIGS. 6 and 7).

Measurements and High Speed Imaging.

Lateral particle migration velocity was calculated from one second fluorescent streak images of 9.9 μm fluorescent beads before and after a single high aspect ratio turn. The distance of the particle center from the inner channel wall before and after the turn was measured. The absolute value of the difference of these distances was divided by an estimated residence time of particles in the turn—the length of the turn along the center of the channel divided by the mean channel velocity. These velocities were confirmed by analyzing images recorded using a Phantom v7.3™ high speed camera (Vision Research, Inc.) and Phantom™ Camera Control software. All high speed images were taken using 1 μs exposure times.

While embodiments have been shown and described, various modifications may be made without departing from the scope of the inventive concepts disclosed herein. The invention(s), therefore, should not be limited, except to the following claims, and their equivalents.

What is claimed is:

1. An inertial particle focusing system for use with a particle having diameter (a), comprising:
   a curved microchannel disposed in a substrate, said microchannel having
   a radius of curvature (r), and
   a channel hydraulic diameter ($D_h$),
   wherein the ratio of r to $D_h$ satisfies the following criterion:

$$2ra^2/D_h^3 \geq 0.037.$$

2. The system of claim 1, wherein the microchannel comprises:
   an inlet;

a curved region; and an outlet.

3. The system of claim 2, wherein the microchannel further comprises:

a filter region; and a straight region.

4. The system of claim 1, wherein the curved region includes a plurality of curves.

5. The system of claim 1, wherein the microchannel has a rectangular cross-section.

6. The system of claim 1, wherein the microchannel has a square cross-section.

7. The system of claim 1, the curved microchannel further comprising an upstream curve and a downstream curve, wherein the upstream and downstream curves have different radii of curvature.

8. The system of claim 7, wherein one of the upstream curve and the downstream curve has a smaller radius and the other has a larger radius, such that a ratio of the larger radius to the smaller radius is greater than 6.

9. A method of focusing particles of diameter a comprising flowing a population of particles within the inertial particle focusing system of claim 1.

* * * * *